United States Patent
Worthen

(10) Patent No.: US 6,585,692 B1
(45) Date of Patent: *Jul. 1, 2003

(54) METHOD AND SYSTEM FOR PATIENT TEMPERATURE MANAGEMENT AND CENTRAL VENOUS ACCESS

(75) Inventor: William J. Worthen, Coto de Caza, CA (US)

(73) Assignee: Alsius Corporation, Irvine, CA (US)

( * ) Notice: Subject to any disclaimer, the term of this patent is extended or adjusted under 35 U.S.C. 154(b) by 55 days.

This patent is subject to a terminal disclaimer.

(21) Appl. No.: 09/839,747

(22) Filed: Apr. 19, 2001

Related U.S. Application Data

(63) Continuation-in-part of application No. 09/253,109, filed on Feb. 19, 1999, now abandoned.

(51) Int. Cl.⁷ .......................... A61F 7/12; A61M 31/00; A61M 37/00
(52) U.S. Cl. .................... 604/113; 604/103.07; 606/22; 607/106
(58) Field of Search ................. 604/113, 507, 604/508, 509, 93.01, 114, 174, 175, 179, 180, 523, 96.01, 101.01, 101.05, 101.03, 102.01–102.03, 103.07, 103.08; 607/104, 105, 106, 21, 23; 606/21–26, 27–31; 137/340, 334

(56) References Cited

U.S. PATENT DOCUMENTS

| | | | | |
|---|---|---|---|---|
| 4,164,943 A | * | 8/1979 | Hill et al. ............ | 128/DIG. 26 |
| 4,820,349 A | | 4/1989 | Saab ..................... | 128/344 |
| 5,246,421 A | | 9/1993 | Saab ..................... | 604/96 |
| 5,261,411 A | * | 11/1993 | Hughes .................. | 600/481 |
| 5,264,260 A | | 11/1993 | Saab ..................... | 428/35.5 |
| 5,269,758 A | * | 12/1993 | Taheri ................... | 604/96.01 |
| 5,337,734 A | | 8/1994 | Saab ..................... | 128/4 |
| 5,342,301 A | | 8/1994 | Saab ..................... | 604/96 |
| 5,358,486 A | | 10/1994 | Saab ..................... | 604/96 |
| 5,411,477 A | | 5/1995 | Saab ..................... | 604/96 |
| 5,443,781 A | | 8/1995 | Saab ..................... | 264/291 |
| 5,499,973 A | | 3/1996 | Saab ..................... | 604/96 |
| 5,569,195 A | | 10/1996 | Saab ..................... | 604/96 |
| 5,624,392 A | | 4/1997 | Saab ..................... | 604/43 |
| 5,755,690 A | | 5/1998 | Saab ..................... | 604/96 |
| 5,837,003 A | | 11/1998 | Ginsburg ................ | 607/106 |
| 5,879,329 A | | 3/1999 | Ginsburg ................ | 604/93 |
| 5,902,268 A | | 5/1999 | Saab ..................... | 604/96 |
| 5,989,238 A | | 11/1999 | Ginsburg ................ | 604/500 |
| 6,004,289 A | | 12/1999 | Saab ..................... | 604/96 |
| 6,019,783 A | | 2/2000 | Philips et al. .......... | 607/105 |
| 6,042,559 A | | 3/2000 | Dobak, III .............. | 604/7 |

(List continued on next page.)

FOREIGN PATENT DOCUMENTS

| | | | | |
|---|---|---|---|---|
| EP | 0 274 411 A2 | 7/1988 | ......... | A61M/29/02 |
| EP | 0 304 258 A3 | 2/1989 | ......... | A61B/17/22 |
| EP | 0 457 456 A1 | 11/1991 | ......... | A61M/25/00 |
| WO | WO 91/17788 | 11/1991 | ......... | A61M/29/00 |
| WO | WO 96/07448 | 3/1996 | ......... | A61M/29/00 |
| WO | WO 98/26831 | 6/1998 | ......... | A61M/25/00 |
| WO | WO 98/31312 | 7/1998 | ......... | A61F/7/12 |
| WO | WO 00/10494 | 3/2000 | ......... | A61F/7/00 |
| WO | WO 00/38601 | 7/2000 | ......... | A61F/7/00 |
| WO | WO 00/47145 | 8/2000 | ......... | A61F/7/00 |
| WO | WO 00/48670 | 8/2000 | ......... | A61N/1/30 |

(List continued on next page.)

*Primary Examiner*—Brian L. Casler
*Assistant Examiner*—Catherine Serke
(74) *Attorney, Agent, or Firm*—John L. Rogitz

(57) ABSTRACT

A catheter with three spiral heat exchange elements surrounding a central supply tube and communicating with a source of heat exchange fluid in a closed loop for effecting patient temperature control and at least two infusion lumens for providing access to the central venous blood supply when the catheter is placed in the central venous system. An anchor can be provided to suture or tape the catheter to the skin of a patient.

13 Claims, 1 Drawing Sheet

U.S. PATENT DOCUMENTS

| | | | |
|---|---|---|---|
| 6,096,068 A | 8/2000 | Dobak, III et al. | 604/105 |
| 6,110,168 A | 8/2000 | Ginsburg | 606/27 |
| 6,126,684 A * | 10/2000 | Gobin et al. | 604/113 |
| 6,146,411 A | 11/2000 | Noda et al. | 607/105 |
| 6,149,670 A | 11/2000 | Worthen et al. | 607/3 |
| 6,149,673 A | 11/2000 | Ginsburg | 607/96 |
| 6,149,676 A | 11/2000 | Ginsburg | 607/106 |
| 6,149,677 A | 11/2000 | Dobak, III | 607/106 |
| 6,165,207 A | 12/2000 | Balding et al. | 607/105 |
| 6,224,624 B1 | 5/2001 | Lasheras et al. | 607/105 |
| 6,231,594 B1 | 5/2001 | Dae | 607/96 |
| 6,231,595 B1 | 5/2001 | Dobak, III | 607/106 |
| 6,235,048 B1 | 5/2001 | Dobak, III | 607/104 |
| 6,238,428 B1 | 5/2001 | Werneth et al. | 607/105 |
| 6,245,095 B1 | 6/2001 | Dobak, III et al. | 607/105 |
| 6,251,129 B1 | 6/2001 | Dobak, III et al. | 607/105 |
| 6,251,130 B1 | 6/2001 | Dobak, III et al. | 607/105 |

FOREIGN PATENT DOCUMENTS

| | | | |
|---|---|---|---|
| WO | WO 00/51534 | 9/2000 | A61F/7/00 |
| WO | WO 00/53135 | 9/2000 | A61F/7/00 |
| WO | WO 00/57823 | 10/2000 | A61F/7/12 |
| WO | WO 00/62837 A3 | 10/2000 | A61B/18/04 |
| WO | wo 00/66053 | 11/2000 | A61F/7/12 |
| WO | WO 00/72779 A2 | 12/2000 | |
| WO | WO 00/72787 A1 | 12/2000 | A61F/7/12 |
| WO | WO 01/03606 A2 | 1/2001 | |
| WO | WO 01/08580 A1 | 2/2001 | |
| WO | WO 01/10323 A1 | 2/2001 | A61B/19/00 |
| WO | WO 01/10365 A1 | 2/2001 | A61F/7/00 |
| WO | WO 01/12061 A1 | 2/2001 | A61B/5/00 |
| WO | WO 01/12122 A2 | 2/2001 | |
| WO | WO 01/13809 A1 | 3/2001 | A61B/18/18 |
| WO | WO 01/13837 A1 | 3/2001 | A61F/7/00 |
| WO | WO 01/17471 A1 | 3/2001 | A61F/7/12 |
| WO | WO 01/19447 A1 | 3/2001 | A61M/31/00 |
| WO | WO 01/26590 A1 | 4/2001 | A61F/7/12 |
| WO | WO 01/30413 A2 | 5/2001 | |

* cited by examiner

METHOD AND SYSTEM FOR PATIENT TEMPERATURE MANAGEMENT AND CENTRAL VENOUS ACCESS

RELATED APPLICATIONS

This is a continuation-in-part of U.S. patent application Ser. No. 09/253,109, filed Feb. 19, 1999 now abandoned, incorporated herein by reference.

FIELD OF THE INVENTION

The present invention relates to methods and systems for patient temperature management.

BACKGROUND OF THE INVENTION

It has been discovered that the medical outcome for a patient suffering from severe brain trauma or from ischemia caused by stroke or heart attack is improved if the patient is cooled below normal body temperature (38° C.). Furthermore, it is also accepted that for such patients, it is important to prevent hyperthermia (fever) even if it is decided not to induce hypothermia.

As recognized by the present invention, the above-mentioned advantages in regulating temperature can be realized by cooling the patient's entire body. Moreover, the present invention understands that since many patients already are intubated with central venous catheters for other clinically approved purposes anyway such as drug delivery and blood monitoring, providing a central venous catheter that can also cool the blood requires no additional surgical procedures for those patients. A cooling central venous catheter is disclosed in the above-referenced parent application.

Other cooling catheters have been disclosed but unfortunately do not recognize the above-noted desirability of combining conventional central venous line functions with a temperature regulation function. The present invention, however, makes this critical observation and provides the solutions set forth herein.

SUMMARY OF THE INVENTION

A central venous access catheter includes a central heat exchange fluid supply lumen terminating at a distal end, and plural heat exchange fluid return tubes communicating with the supply lumen at the distal end and carrying heat exchange fluid in a closed circuit. Each return tube is formed spirally around the supply lumen such that a body fluid flowing past the return tube exchanges heat with the fluid flowing therein. The catheter also defines at least two infusion lumens separated from the heat exchange fluid and terminating in respective ports that are longitudinally separated from each other. With this structure, each infusion lumen provides access to the central venous blood supply of a patient when the catheter is placed in the central venous system of a patient. In one preferred embodiment, an anchor is located proximal to at least one return tube and is configured for affixing the catheter to the skin of a patient.

In another aspect, a central venous access catheter includes a central heat exchange fluid supply lumen terminating at a distal end, and plural heat exchange fluid return tubes communicating with the supply lumen at the distal end and carrying heat exchange fluid in a closed circuit. Each return tube is formed spirally around the supply lumen such that a body fluid flowing past the return tube exchanges heat with the fluid flowing therein. An anchor can be located proximal to at least one return tube and can be configured for affixing the catheter to the skin of a patient.

In still another aspect, a central venous catheter includes at least first and second hollow spiral-shaped heat exchange elements. Each heat exchange element conveys a heat exchange fluid for exchanging heat with a body fluid flowing past the element. At least one closed circuit fluid pathway conveys heat exchange fluid to and from the heat exchange elements, and at least first and second infusion lumens are separated from the heat exchange fluid and terminate in respective ports that are longitudinally separated from each other. Each infusion lumen provides access to the central venous blood supply of a patient when the catheter is placed in the central venous system of a patient.

In yet another aspect, a central venous catheter includes first, second, and third hollow corkscrew heat exchange elements, a closed circuit fluid pathway for conveying heat exchange fluid to and from the heat exchange elements, and an anchor located proximal to at least one heat exchange element and configured for affixing the catheter to the skin of a patient.

In another aspect, a method for treating a patient includes advancing a catheter into the central venous system of the patient and circulating a heat exchange fluid through the catheter to exchange heat with the patient. Simultaneously with the circulating act, one or more central venous (CV) line functions is undertaken using the catheter.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
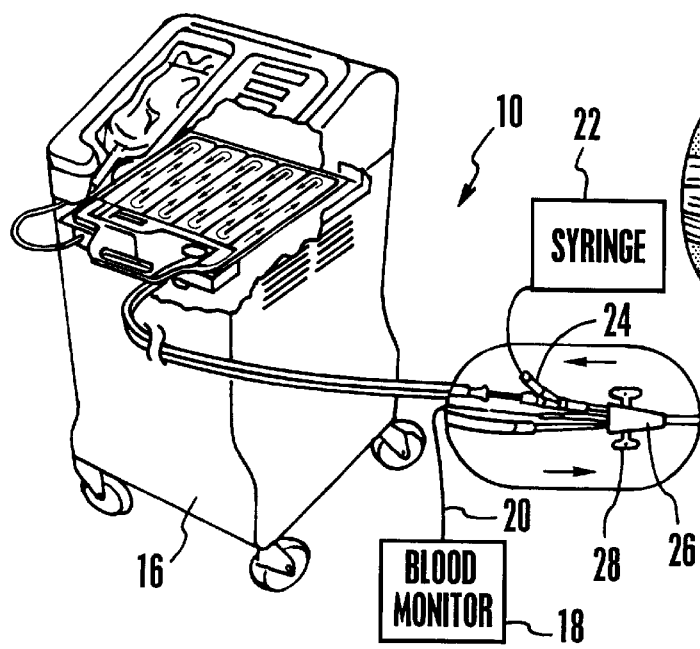
FIG. 1 is a schematic view of the central venous access catheter, with portions enlarged and other portions broken away for clarity.

Referring initially to FIG. 1, a system, generally designated 10, is shown for managing and otherwise controlling patient temperature while providing access to the central venous system of a patient. As shown, the system 10 includes a central venous access and heat exchange catheter 14 that receives a heat exchange fluid (also referred to herein as "coolant") from a heater/chiller 16, with the fluid circulating in a closed loop. The fluid can be saline or other fluid such as refrigerant, and the heater/chiller 18 can be made by, e.g., the present assignee or by Radiant Medical Corp. of Redwood City, Calif. Either the fluid flow rate and/or the temperature of the fluid is controlled by a controller associated with the heater/chiller 16 based on a patient temperature feedback signal to control the amount and if desired the rate at which heat is added or subtracted from the patient. The controller can be implemented by a software-executing processor or by discrete logic circuits or other electronic circuitry device to establish a desired patient temperature by appropriately controlling the flow rate and/or heat exchanger in response to a temperature signal derived from a sensor in the patient.

As also shown in FIG. 1, at least two central venous (CV) components can be in communication with the catheter 16 for undertaking central venous functions in addition to controlling the temperature of the patient. These functions include and are not limited to drug infusion and blood extraction for blood monitoring, as well as blood pressure monitoring. For instance, a blood monitor 18 can communicate with the catheter 14 via a line 20 to monitor blood pressure or withdraw blood from the central venous system of the patient. Also, a syringe 22 can engage the catheter 14 via a connector 24 such as a Y-type connector for infusing drugs or other medicament such as epinephrine into the patient.

The components 16, 18, 22 can all be connected to the catheter 14 via a proximal connector hub 26 of the catheter 14. The hub 26 can be formed with a suture anchor 28 or other anchor structure such as tape for providing a means to fasten the catheter 14 to the skin of the patient for long-term use.

Figure 2:
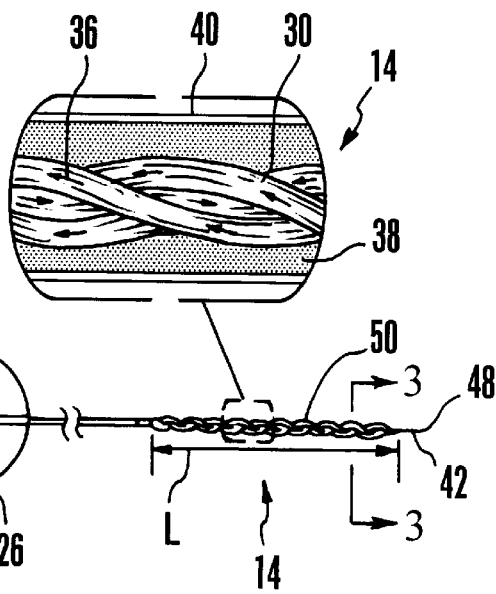
FIG. 2 is an enlarged perspective view of a portion of the central venous access catheter shown in FIG. 1.
Figure 3:
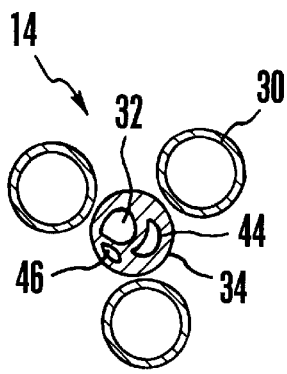
FIG. 3 is a cross-sectional view as seen along the line 3—3 in FIG. 1.

As shown in cross-reference to FIGS. 1–3, the catheter 14 can include plural heat exchange elements 30. The heat exchange elements 30 can be established by, e.g., three coolant return tubes made of hollow plastic, with each tube establishing a respective coolant return lumen. As shown best in FIG. 3, a central coolant supply lumen 32 that is established by a center tube 34 is also provided. It is to be understood that the supply lumen 32 conveys coolant from the heater/chiller 16 in a distal direction along the catheter 14, whereas the heat exchange elements 30 (the coolant return tubes) convey coolant back to the heater/chiller 16 in a proximal direction as indicated by the arrows 36 in FIG. 2. With this structure, blood 38 in a central venous system vein 40 into which the catheter 14 is advanced is cooled (or heated) by exchanging heat with the coolant across the walls of the heat exchange elements 30. Thus, coolant is circulated in a closed fluid communication loop between the heat exchange elements 30 and heater/chiller 16 to remove heat from the patient or to add heat to the patient to rewarm the patient after surgery or after the termination of therapeutic hypothermia treatment.

The coolant return tubes are spirally formed around the center tube 34, and can be adhered thereto or not. That is, the preferred heat exchange elements 30 define spirals. The length "L" of the heat exchange region of the catheter 14 can be about 250 millimeters, with the pitch of the spiral heat exchange elements 30 being about 64 millimeters. In any case, the coolant supply lumen 32 terminates in a hollow distal tip 42, as do the lumens of the heat exchange elements 30. Accordingly, coolant passes from the supply tube to the return tubes at the distal tip 42.

Additionally, as best shown in FIG. 3, the center tube 34 can establish one or more working lumens (only two shown in FIG. 3 for clarity of disclosure) for undertaking CV functions simultaneously with controlling patient temperature. In the embodiment shown, the center tube 34 establishes first and second working lumens 44, 46 that have any suitable cross-sectional shape and that can respectively communicate with the central venous components 18, 22 discussed above. Both working lumens 44, 46 are separated from the coolant and both working lumens preferably extend to the hub 26 shown in FIG. 1. The working lumens 44, 46 can terminate in respective exit ports 48, 50 (FIG. 1), with the ports 48, 50 preferably being longitudinally spaced from each other. For instance, the port 48 can be at the end of the distal tip 42 of the catheter 14 as shown, and the port 50 located somewhat proximal to the tip 42 to provide for mixing of infused drugs in the bloodstream if two drugs are to be administered. With the above in mind, the monitor 18 (FIG. 1) or other CV device such as an infusion device can communicate with one of the infusion or working lumens 44, 46 while the syringe 22 can communicate with the other infusion or working lumen 46, 44.

Figure 4:
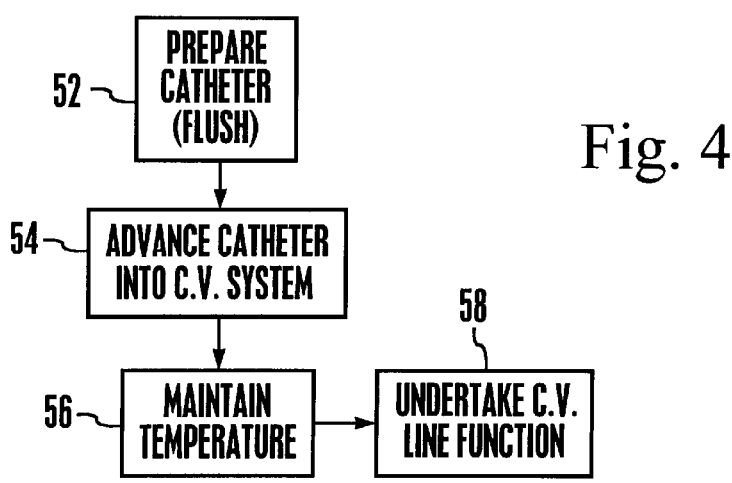
FIG. 4 is a flow chart of the method for using the catheter shown in FIG. 1.

Referring to FIG. 4, the catheter 14 is first prepared for use by, e.g., flushing one or more of the lumens with saline at block 52. Then, at block 54 the heat exchange portion of the catheter 14 is advanced (possibly through an introducer sheath) into the vena cava of the patient through a groin entry point or through a neck entry point to the central venous system of the patient. When advanced through the groin the catheter is advanced either through the saphenous vein or femoral vein to the inferior vena cava, and when advanced through the neck through the jugular or subclavian vein to the superior vena cava or inferior vena cava. At block 56, patient temperature is established and/or maintained at normothermia or at a hypothermic temperature as desired by appropriately inputting a desired temperature to the heater/chiller 16. Simultaneously with temperature control, central venous line functions are undertaken at block 58.

While the particular METHOD AND SYSTEM FOR PATIENT TEMPERATURE REGULATION AND CENTRAL VENOUS ACCESS as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for".

What is claimed is:

1. A central venous access catheter, comprising:
    a central heat exchange fluid supply lumen terminating at a distal end;
    plural heat exchange fluid return tubes communicating with the supply lumen at the distal end for carrying heat exchange fluid, each return tube being formed spirally around the supply lumen such that a body fluid flowing past the return tube exchanges heat with the heat exchange fluid flowing therein; and
    the catheter also defining at least two infusion lumens separated from the heat exchange fluid and terminating in respective ports longitudinally separated from each other, each infusion lumen providing access to the central venous blood supply of a patient when the catheter is placed in the central venous system of a patient.

2. The catheter of claim 1, further comprising an anchor located proximal to at least one return tube and configured for affixing the catheter to the skin of a patient.

3. The catheter of claim 1, comprising three return tubes.

4. A central venous catheter, comprising:
   at least first and second hollow spiral-shaped heat exchange elements, each being configured for conveying a heat exchange fluid for exchanging heat with a body fluid flowing past the element;
   at least one fluid pathway for conveying heat exchange fluid to and from the heat exchange elements; and
   at least first and second infusion lumens separated from the heat exchange fluid and terminating in respective ports longitudinally separated from each other, each infusion lumen providing access to the central venous blood supply of a patient when the catheter is placed in the central venous system of a patient.

5. The catheter of claim 4, further comprising an anchor located proximal to at least one heat exchange element and configured for affixing the catheter to the skin of a patient.

6. The catheter of claim 4, comprising three heat exchange elements.

7. A method for treating a patient, comprising:
   advancing a catheter into the central venous system of the patient;
   circulating a heat exchange fluid through the catheter to exchange heat with the patient by removing heat from the patient; and
   simultaneously with the circulating act, undertaking one or more central venous (CV) line functions.

8. The method of claim 7, wherein the catheter has at least one spirally configured heat exchange element.

9. The method of claim 8, wherein the element conveys heat exchange fluid in a proximal direction relative to the catheter.

10. The method of claim 7, wherein the CV function is medicament infusion.

11. The method of claim 7, wherein the CV function is blood monitoring.

12. The method of claim 7, comprising undertaking at least two CV functions.

13. A central venous catheter, comprising:
    at least first, second, and third hollow corkscrew heat exchange elements establishing at least part of at least one closed circuit fluid pathway for a heat exchange fluid; and
    at least first and second infusion lumens separated from the heat exchange fluid and terminating in respective ports longitudinally separated from each other, each infusion lumen providing access to the central venous blood supply of a patient when the catheter is placed in the central venous system of a patient.

* * * * *